United States Patent [19]

Coss et al.

[11] Patent Number: 5,100,321
[45] Date of Patent: Mar. 31, 1992

[54] DENTAL TOOL

[76] Inventors: Ronald G. Coss, 30 Hillsdale, Newport Beach, Calif. 92660; Bernard G. Gantes, 315 Clipper Way, Seal Beach, Calif. 90740

[21] Appl. No.: 516,723

[22] Filed: Apr. 30, 1990

[51] Int. Cl.⁵ .......................... A61C 1/07; A61C 3/03; A61C 3/08
[52] U.S. Cl. .................... 433/118; 433/125; 433/147
[58] Field of Search ............ 433/118, 119, 124, 125, 433/141, 142, 143, 144, 147; 81/3.8, 9.4, 44; 254/28, 18, 25; 29/242

[56] References Cited

U.S. PATENT DOCUMENTS

| Re 30,536 | 3/1981 | Perdreaux, Jr. | 433/86 |
|---|---|---|---|
| 1,454,239 | 5/1923 | Kawamura | 254/25 |
| 1,586,302 | 5/1926 | Funk | 433/141 X |
| 1,886,155 | 11/1932 | Bohlman | 81/3.8X |
| 2,016,597 | 10/1935 | Drake | 433/142 |
| 2,677,843 | 5/1954 | Goodman | 433/143 |
| 3,522,801 | 8/1970 | Robinson | 433/119 X |
| 3,645,255 | 2/1972 | Robinson | 433/119 X |
| 3,987,549 | 10/1976 | Robertelli | 433/166 X |
| 4,219,619 | 8/1980 | Zarow | 433/118 |
| 4,289,486 | 9/1981 | Sargeant | 433/118 |
| 4,422,489 | 12/1983 | Ross | 81/44 |
| 4,913,133 | 4/1990 | Tichy | 433/142 |
| 4,939,959 | 7/1990 | Rokita | 81/44 |
| 4,946,389 | 8/1990 | Weissenburger | 433/142 |

FOREIGN PATENT DOCUMENTS 1097957  3/1981  Canada .................. 433/142

*Primary Examiner*—Robert P. Swiatek
*Assistant Examiner*—Nicholas D. Lucchesi
*Attorney, Agent, or Firm*—Knobbe, Martens, Olson & Bear

[57] ABSTRACT

A dental apparatus for cleaning teeth includes a metallic scaling element formed to receive a slender, rigid, smooth plastic sheath. The scaling element is vibrated by a sonic generator, causing its outer sheath to vibrate as well. The sheath or tip is composed of a material such as polysulfone having good thermal stability for covering the tip of the metallic scaling element. The small diameter free end of the sheath is especially useful in the removal of plaque from an individual's teeth or titanium implants while preventing damage to the surface of the teeth or implants.

14 Claims, 3 Drawing Sheets

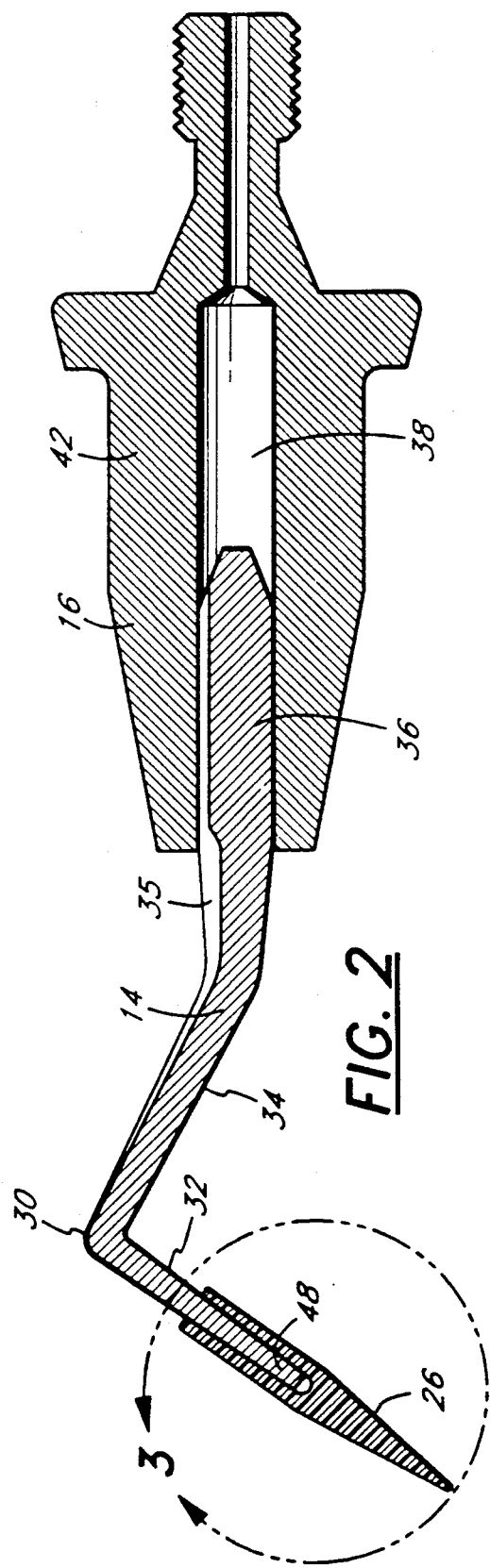
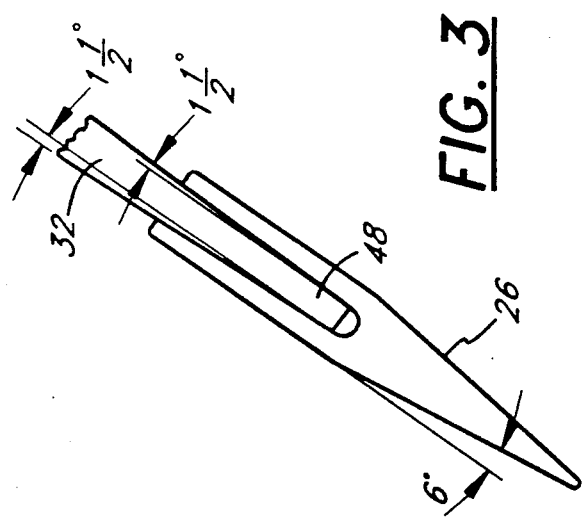
FIG. 2
FIG. 3

DENTAL TOOL

FIELD OF THE INVENTION

This invention relates to dental apparatus and, particularly, to an instrument for cleaning teeth and dental implants in a non-abrasive manner.

BACKGROUND ON THE INVENTION

Currently, teeth are primarily cleaned by dental hygienists and dentists utilizing hand-operated cleaning tools or a mechanized tool wherein the cleaning element is vibrated at sonic frequencies. A disadvantage of present tools is that their typically metal, cleaning elements have relatively sharp edges that can damage or scrape away enamel or dentin from the tooth. Also, sharp edges can chip crown or composite resin margins.

Recently, tooth implants have been developed wherein a missing tooth is replaced by a prosthesis which is implanted in the jaw. The composition of the implant is such that the bone tissue will actually attach to the implant so that it is firmly anchored. This eliminates the need for a bridge wherein an artificial tooth is not positioned within the jawbone but, instead, is anchored to adjacent teeth.

It is necessary to clean plaque and scale from the implant, just as a natural tooth, particularly beneath the gum line. Unfortunately, the material employed for the implants is damaged by conventional scaling tools. Commonly, the implant is made of titanium and is highly polished. The sharp metal edge of the scaling tool roughens and mars the surface of the implant, thereby increasing the surface area available for the adherence of unwanted plaque.

Accordingly, a need exists for a tool which will properly clean tooth implants, as well as natural teeth, without damaging the surface of the teeth, and clean crown and restoration margins.

SUMMARY OF THE INVENTION

It is an object of the invention to provide an improved tooth-cleaning tool which will not scratch the surface of tooth implants or natural teeth. According to the present invention, a metallic scaling element attached to a sonic vibrator is covered by a thin, replaceable, nonmetallic sheath or tip. In a preferred embodiment, the tip of a metallic scaling element is made shorter than a conventional element; and, rather than having sharp edges, it is smooth and generally frusto-conical in shape with a slight taper towards the free end. The configuration of the non-metallic tip is complementary to the metallic scaling element, being formed with a socket having mating tapered surfaces which provide considerable contact with the metal element. As a result, the non-metallic tip is securely attached to the metallic element simply by pressing it into position. Preferably, the included angle on the tip of the metallic element and on the interior of the mating socket on the non-metallic sheath is about 3°, or about 1½° with respect to the axis of the components.

The exterior is preferably cylindrical in the area of the socket, but then is generally conical or frusto-conical tapering to a small-diameter, smoothly-rounded free end. It is this tapered surface which contacts a tooth and provides the cleaning surface. Preferably, the tip exterior tapers at an angle of about 6°, with respect to the axis, to a free end of about 0.030 inches in diameter, rounded on the end with a radius of about 0.015 inches.

The non-metallic tip is preferably composed of a rigid but strong plastic such as polysulfone. The smoothly curved vibrating tip is somewhat resilient and does not mar the surface of teeth. Polysulfone offers useful properties, such as maintaining thermal stability and rigidity at temperatures up to 300° F. This feature is of great significance since dental devices acting at sonic frequencies generate excessive heat which, if not addressed, may distort the properties of a thermally unstable device. Yet, it has been found that an all-plastic tool cannot satisfactorily support itself, even if cooling is provided. The plastic tip on a metal tool works very satisfactorily with cooling.

Since the plastic tip is quite small and, therefore, not easy to handle, a preferred method of removal is accomplished by employing a special tool. This tool includes a notch for receiving the removable tip with the shank of the metal-supporting element positioned in a slot open to the notch. Upon pulling this special tool away from the cleaning tool, the plastic tip is captured within the confines of the notch, thereby removing the tip from the cleaning tool.

BRIEF DESCRIPTION OF THE DRAWINGS

FIG. 2 is a cross-sectional view of the tool of FIG. 1.

FIG. 3 is an enlarged schematic view of the replaceable non-metallic tip and a portion of the metallic scaling element.

DETAILED DESCRIPTION OF THE PREFERRED EMBODIMENT

Figure 1:
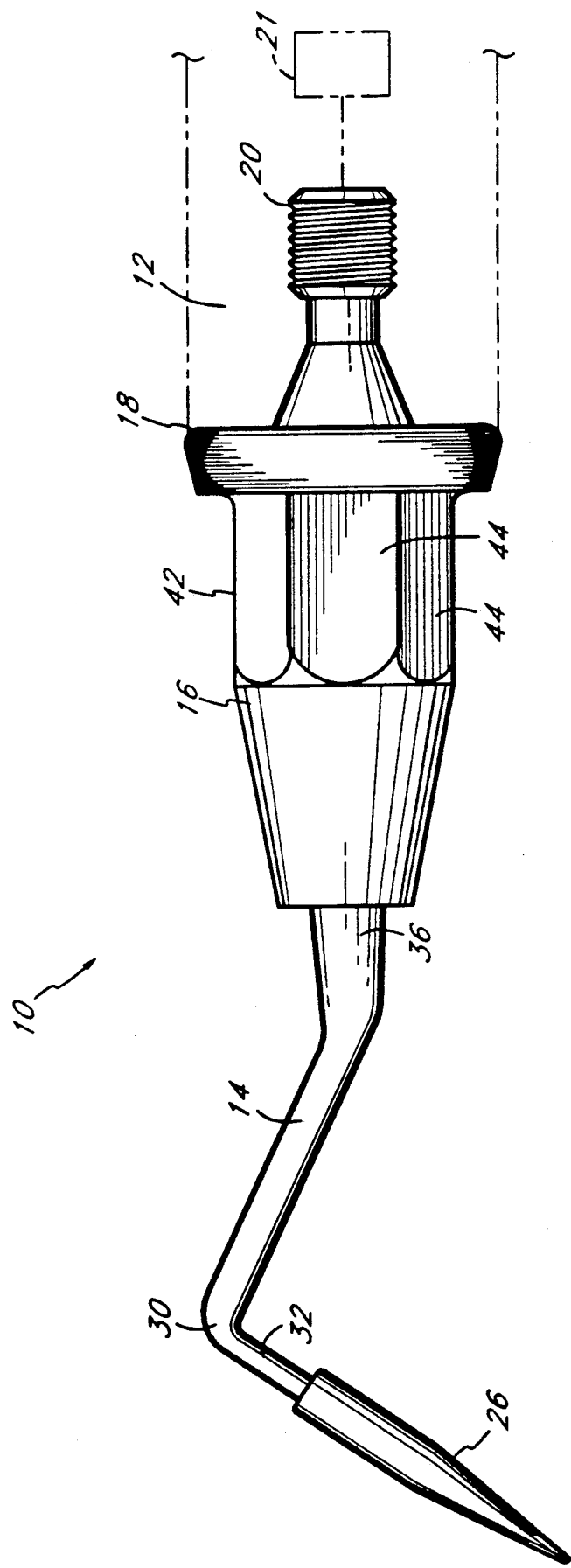
FIG. 1 is a side elevational view of a sonic cleaning tool with the non-metallic tip of the present invention positioned on a metallic scaling element.

Referring to FIG. 1, there is shown a sonic tooth-cleaning device 10, including a cylindrical housing 12, shown in phantom lines, and attached on one end to a sleeve or base 16, which supports a metallic scaling element 14. The external threading on a rearwardly extending portion 20 of the base 16 is used to connect the scaling element to a source of coolant (not shown) and a schematically-shown sonic generator 21. Such a device is not illustrated in detail in that it is well known that the sonic generator provides sonic vibrations to produce vibratory movement to the metallic scaling element 14 in the removal of plaque from teeth.

The present invention provides a plastic or nonmetallic sheath or tip 26 positioned on the tip of the cleaning element 14. The tip 26 is preferably made of a rigid, thermally stable plastic material, such as polysulfone. In utilizing the tool, the polysulfone material engages the tooth during a cleaning operation and, thus, prevents the metallic scaling element from scraping the surface of teeth or polished titanium implants which are easily scratched. Polysulfone is a desirable material to use for this purpose due to its high strength and its ability to withstand significant heat.

FIG. 1 illustrates a metal scaling element, which is similar to a conventional one except for its having a special tip. As seen in FIG. 1 and FIG. 2, the element includes a hook-shaped section 30 consisting of a front or free end section 32 which meets an adjoining rear section 34 at an angle of about 100°. This angle is desirable in that it enables the dentist to better manipulate the tool for difficult-to-reach areas inside the mouth. Section 34 merges with a shank portion 36, which is shaped to be received within an elongated cavity or bore 38 in the base 16, as seen in FIG. 3. A groove 35 is shown in FIG. 2 in the top portion of the sections 36 and 34 to conduct coolant to the tip. The rear portion of that groove is connected to a source of coolant (not shown) through the housing 12.

Referring to FIGS. 2 and 3, the free end of the scaling element section 32 has a smooth frusto-conical shape with approximately a 3° converging taper extending in the direction of its free end. That is, the exterior of the free end forms a 1½° angle with the longitudinal axis of the element 14. This is in contrast to the sharp edges formed on the conventional scaling elements which typically have a square or triangular shaped cross-section. Also, the free end is shorter than a conventional element since it is to support a tip which, when combined with the metal element, is comparable in length to a conventional element.

The non-metallic tip 26 has a bore or socket in its rear end, which also has an included angle taper of approximately 3°, that mates with the taper on the metallic tip 48. The components are dimensioned such that the extreme end of the metallic tip 48 does not normally bottom out or engage the end of the socket in the tip 26. This ensures that the exterior of the metallic tip 48 engages the socket walls of the non-metallic tip 26, providing good frictional engagement, such that the non-metallic tip is firmly attached to the metallic element and will not slip or become unattached during operation.

The socket in the non-metallic tip extends for a little less than half of the length of the tip 26. Thus, the free end of the tip 26 relies upon its own rigidity for support. As indicated above, an all-plastic scaling element becomes too hot during the operation of the sonic cleaning tool such that it does not maintain sufficient rigidity. However, with the combination illustrated, the metal tip provides the necessary strength and further assists in conducting heat away to the coolant, which flows through the groove 35 to bathe the tool tip during operation.

The dimensions of the plastic tip 26 in a preferred form of the invention illustrate the small size of the tip. The rear portion of the plastic tip is substantially cylindrical, with a diameter approximately 0.090 inch, with the wall thickness increasing towards the closed end of the overall length of the plastic tip is about 0.50 inches, with the socket being a little less than half of that length and the remaining free end of the tip 26, therefore being a little more than half. The exterior of the free end of the tip tapers at about 6° from the cylindrical portion to a diameter of about 0.30 inches at its closed end in a preferred arrangement. The free end is substantially rounded in a radius of about 0.015 inches in a preferred system. The small size enables the free end to fit into crevices between adjacent teeth and to extend between the gum and the base of the tooth. As indicated above, the smooth surface of the non-metallic tip 26, which is softer than the metallic element, does not mar or otherwise damage the exterior of the tooth or an implant, and yet the surface is effective for removing plaque. Although the non-metallic tip is possibly durable enough to withstand more than one use, its cost is such that it is practical to dispose of it after each use. This is highly desirable because of the concern of orally communicable diseases.

Figure 4A:
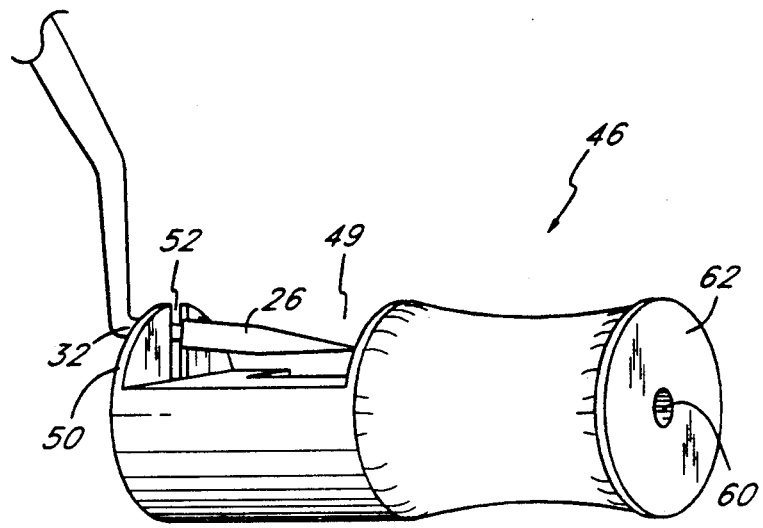
FIG. 4a is a perspective view of the tip tool used for removal of the non-metallic tip from the metallic scaling element.
Figure 4B:
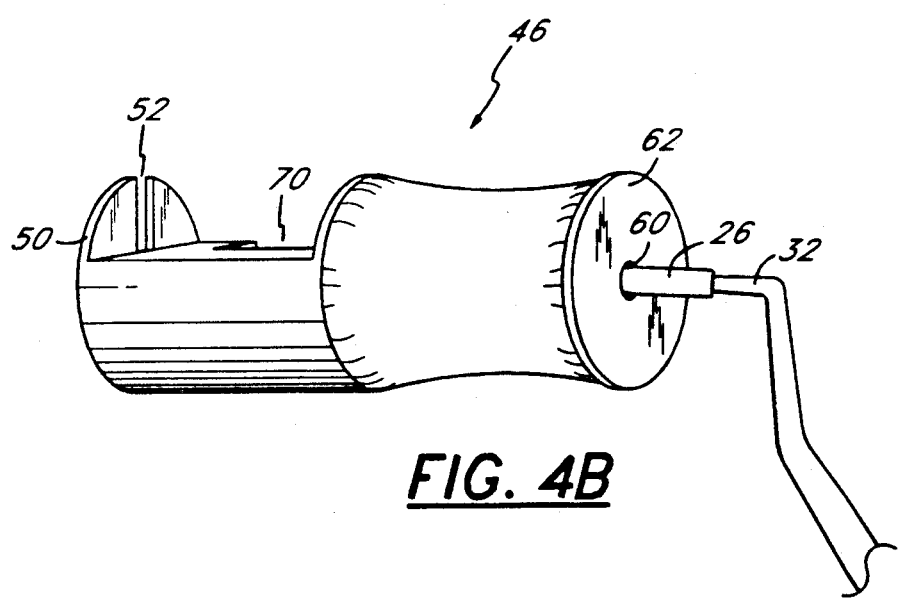
FIG. 4b is a perspective view of the tip tool used for insertion of the metallic scaling element into the nonmetallic tip.

To assist in the removal and replacement of the non-metallic tip 26 in the dentist's office, there is provided a special tool 46, as illustrated in FIGS. 4a and 4b. The tool has a generally cylindrical shape. However, a large notch 49 is formed in the top half of the front portion of the tool, as viewed in the drawings. This notch 49 extends axially sufficiently far to receive the length of plastic tip 26 of the tool 10, as seen in FIG. 4a. The end wall 50 of the tool, forming one boundary for the notch 49, has a vertically extending slot 52 that opens outwardly or upwardly as shown. The width of the slot 52 is sufficient to receive the metallic scaling element in the area adjacent the rear of the non-metallic tip, but the width is less than the rear diameter of the non-metallic tip. With this relationship, the non-metallic tip may be positioned within the notch 49, and the adjacent portion of the metallic element can fit within the slot 52. The non-metallic tip is thus captured within the notch 49. By pulling on the cleaning device and the tip tool in a manner to separate the components, the metallic scaling element 14 is separated from the tool and the non-metallic tip 26, which remains captured within the tip tool notch 49.

As another feature, the tip tool 46 is useful to install the tiny tip on the metal element. A cylindrical bore or socket 60 is formed in the other end of the tool, opening to the end surface 62. This socket 60 is dimensioned to receive the non-metallic tip, and the length of the non-metallic tip is greater than the length of the socket such that the tip end engages the inner end of the socket 60 while the rear of the tip extends beyond the rear face, as shown in FIG. 4b. The diameter of the socket 60 is sized to properly support the non-metallic tip within the recess, but at the same time it is large enough so that friction does not result between the non-metallic tip and the interior surface of the socket 60. Thus, by positioning a non-metallic tip in the socket 60, the tip of the metallic scaling element 14 can be readily inserted into the non-metallic tip.

As a further feature, the tip tool 46 is also designed for use as a small wrench in separating the base 16 from the cylindrical housing 12. A cut-out 70 is formed in the side wall of the forward portion of the tool 46. The width of the cut-out is dimensioned to fit onto the flats 44 of the exterior of the housing portion 42.

We claim:
1. A dental tooth cleaning tool comprising a slender but rigid metal tooth cleaning element for connection on one end to a vibrator to vibrate the element at sonic frequencies, and a plastic tip member having a rear end with a socket formed therein, the socket having an end that opens to the rear of said member and that fits onto a free end of said element, said member having a self-supporting free end extending forwardly beyond the socket having an exterior surface to vibrate against the surface of a tooth to remove plaque, said element free end being solid and nontubular so as to have sufficient strength for plaque removal operations, the free end of said tip member having a smoothly curved exterior which does not mar or scratch the surface of the tooth and said tip member, except for said socket, being imperforate and made of plastic material which is rigid and strong and sufficiently thermally stable to with- stand the heat generated during use of the tool engaging a tooth.

2. The tool of claim 1 wherein the free end of said element has an exterior surface which tapers slightly in the direction of its free end to a smaller cross section, and said socket has a similar taper.

3. The tool of claim 2 wherein said element free end exterior surface tapers to form an included angle of about 3° about a longitudinal axis of said element.

4. The tool of claim 1 wherein the free end of said element has a frusto-conical configuration with a slight taper to a reduced diameter at the tip of the element free end, and said plastic socket has a frusto-conical shape with a taper similar to that on said element so that the socket fits snugly and smoothly onto the free end of the metallic element.

5. The tool of claim 1 wherein the plastic tip member is composed of a material which is thermally stable up to 300° F., such as polysulfone.

6. The tool of claim 1 wherein said tip member has an end portion which extends beyond said element free end, a distance about equal to the length of said socket.

7. The tool of claim 1 wherein said plastic tip member is about ⅛ inch in length, has an outer diameter in the area of said socket of about 0.08 inches, which tapers to a free end diameter of about 0.03 inches.

8. The tool of claim 7 wherein said tip member free end is rounded, with a radius of about 0.015 inches.

9. The tool of claim 7 wherein said plastic tip member tapers on is exterior at about 6° with respect to a longitudinal axis of said element end and said plastic tip member.

10. The tool of claim 1 wherein said element has an exterior coolant passage for conducting coolant along the exterior of the element and to the exterior of said tip member.

11. A dental tooth cleaning tool comprising:
a vibrator capable of vibrating at sonic frequencies;
a slender but rigid metal tooth cleaning element connected at one end to said vibrator to vibrate the element at sonic frequencies; and
a plastic tip member having a rear end with a socket formed therein, the socket having an end that opens to the rear of said member and that fits onto a free end of said element, said member having a self-supporting free end extending forwardly beyond the socket and having an exterior surface to vibrate against the surface of a tooth to remove plaque,
said element free end being solid and non-tubular so as to have sufficient strength for plaque removal operations;
the free end of said tip member having a smoothly curved exterior which dies not mar or scratch the surface of the tooth, and said tip member free end being imperforate on its exterior and made of plastic material which is rigid and strong and sufficiently thermally stable.

12. A combination, comprising:
a dental tooth cleaning tool comprising a slender but rigid metal tooth cleaning element for connection on one end to a vibrator to vibrate the element at sonic frequencies, and a plastic tip member having a rear end with a socket formed therein, the socket having an end that opens to the rear of said member and fits onto a free end of said element, said member having a self-supporting free end extending forwardly beyond the socket and having an exterior surface to vibrate against the surface of a tooth to remove plaque, said member free end being solid and non-tubular so as to have sufficient strength for plaque removal operations, the free end of said tip member having a smoothly curved exterior which does not mar or scratch the surface of a tooth, and said tip member being made of plastic material which is rigid and strong and sufficiently thermally stable to withstand the heat generated during use of the tool; and
an installation tool having a cylindrical cavity to receive the free end of the plastic tip member while the socket open end extends outwardly to receive said metallic element.

13. The combination of a dental tooth cleaning tool and an installation tool for the cleaning tool comprising:
a dental tooth cleaning tool comprising a slender but rigid metal tooth cleaning element for connection on one end to a vibrator ti vibrate the element at sonic frequencies, and a plastic tip member having a rear end with a socket formed therein, the socket having an end that opens to the rear of said member and fits onto a free end of said element, said member having a self-supporting free end extending forwardly beyond the socket and having an exterior surface to vibrate against the surface of a tooth to remove plaque, said member free end being solid and non-tubular so as to have sufficient strength for plaque removal operations, the free end of said tip member having a smoothly curved exterior which does not mar or scratch the surface of a tooth, and said tip member being made of plastic material which is rigid and strong and sufficiently thermally stable to withstand the heat generated during use of the tool; and
an installation tool having a slot which is slightly larger than the diameter of said metal element adjacent said tip member and is slightly smaller than the outside diameter of the tip member adjacent said element, whereby the tip member may be separated from the element by placing the element in the slot and applying a separating force to the plastic tip and metal element.

14. A method of removing plaque from teeth, comprising:
placing against the surface of a tooth to be cleaned a plastic tip member mounted on a free end of a slender but rigid metal tooth cleaning element having its other end connected to a vibrator, said element free end being solid and non-tubular so as to have sufficient strength for plaque removal operations, said tip member having a self-supporting free end extending forwardly beyond said element and having a smoothly curved exterior which does not mar or scratch the surface of a tooth, said tip member free end being imperforate on its exterior and made of plastic material which is rigid and strong and sufficiently thermally stable to withstand the heat generated during vibration of said element; and
vibrating the tool sonically while the tip member engages the tooth.

* * * * *